US008695206B2

(12) United States Patent  
Isaacson et al.

(10) Patent No.: US 8,695,206 B2
(45) Date of Patent: Apr. 15, 2014

(54) TISSUE CLAMP FOR NONINVASIVE PHYSIOLOGICAL MEASUREMENT

(75) Inventors: Philip O. Isaacson, Chanhassen, MN (US); Bryant Austin Jones, Minnetonka, MN (US); Timothy L. Johnson, Plymouth, MN (US); Christopher Holland, Mayer, MN (US); Matthew Prior, Plymouth, MN (US)

(73) Assignee: Nonin Medical, Inc., Plymouth, MN (US)

( * ) Notice: Subject to any disclaimer, the term of this patent is extended or adjusted under 35 U.S.C. 154(b) by 0 days.

(21) Appl. No.: 13/457,036

(22) Filed: Apr. 26, 2012

(65) Prior Publication Data

US 2012/0289800 A1 Nov. 15, 2012

Related U.S. Application Data

(60) Provisional application No. 61/479,544, filed on Apr. 27, 2011.

(51) Int. Cl.
*H05K 13/00* (2006.01)
*A61B 5/1455* (2006.01)

(52) U.S. Cl.
USPC .......................................... 29/592.1; 600/344

(58) Field of Classification Search
USPC ............ 600/310, 322, 323, 344, 549; 29/592, 29/592.1, 428
See application file for complete search history.

(56) References Cited

U.S. PATENT DOCUMENTS

| 3,810,460 A | * | 5/1974 | Van Nie ........................ 600/479 |
| 5,957,840 A | * | 9/1999 | Terasawa et al. ............. 600/310 |
| 6,154,667 A | * | 11/2000 | Miura et al. .................. 600/323 |
| 2007/0260131 A1 | | 11/2007 | Chin |
| 2010/0210924 A1 | | 8/2010 | Parthasarathy et al. |

FOREIGN PATENT DOCUMENTS

| DE | 102008007337 B3 | 10/2009 |
| WO | WO-2006009906 A2 | 1/2006 |
| WO | WO-2008154020 A1 | 12/2008 |
| WO | WO-2012149168 A1 | 11/2012 |

OTHER PUBLICATIONS

"International Application Serial No. PCT/US2012/035224, International Search Report mailed Jul. 9, 2012", 5 pgs.
"International Application Serial No. PCT/US2012/035224, Written Opinion mailed Jul. 9, 2012", 6 pgs.

* cited by examiner

*Primary Examiner* — Eric Winakur
(74) *Attorney, Agent, or Firm* — Schwegman, Lundberg & Woessner, P.A.

(57) ABSTRACT

A device includes a clamp and a sensor. The sensor can be attached to the clamp and tissue by the force exerted by the clamp. The clamp includes a first jaw member having a jaw face and a second jaw member having a complementary face. The first and second jaw members are held in alignment by a joint. The joint has an elastic member configured to exert a compressive force. The joint allows movement of the jaw face relative to the complementary face in directions corresponding to pitch, roll, yaw, and heave. The compressive force is distributed over a surface of the jaw face. The sensor is coupled to the jaw face or held in place by the compressive force of the jaw face. The sensor is configured to generate a sensor signal corresponding to a physiological parameter of tissue proximate the jaw face.

8 Claims, 14 Drawing Sheets

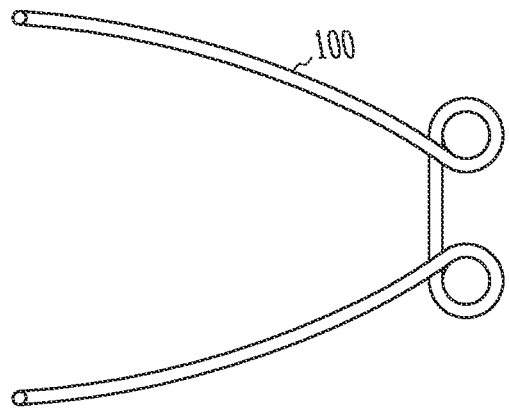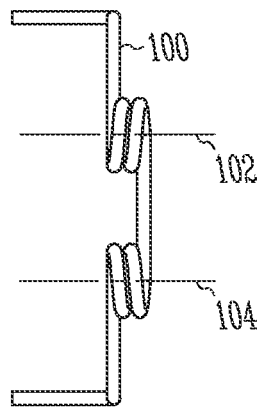
Fig. 4A    Fig. 4B
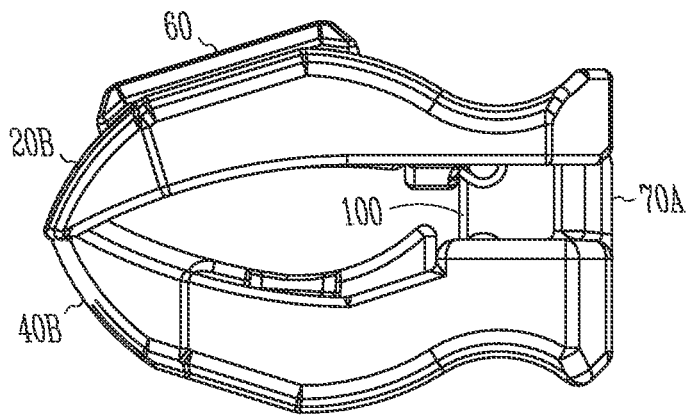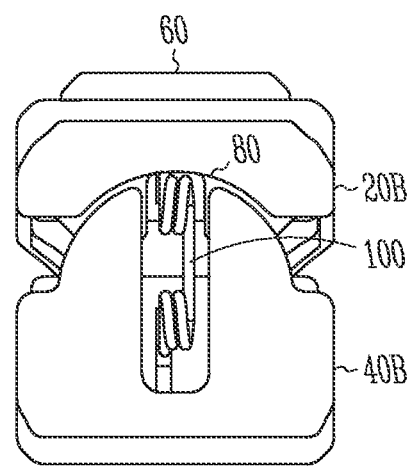
Fig. 5A    Fig. 5B

TISSUE CLAMP FOR NONINVASIVE PHYSIOLOGICAL MEASUREMENT

CLAIM OF PRIORITY

This patent application claims the benefit of priority, under 35 U.S.C. Section 119(e), to Philip O. Isaacson, U.S. Provisional Patent Application Ser. No. 61/479,544, entitled "TISSUE CLAMP FOR NONINVASIVE PHYSIOLOGICAL MEASUREMENT," filed on Apr. 27, 2011, which is hereby incorporated by reference herein in its entirety.

BACKGROUND

The shape of many areas of the human body is complex and can vary considerably from one individual to another. As such, for some non-invasive physiological measurements, the industry has turned to adhesively-applied sensors. Adhesively-applied sensors have various problems and limitations. An adhesively-applied sensor cannot be easily repositioned and may have an adhesive bond that is compromised. In addition, adhesively-applied sensors do not adhere well to some subjects or measurement sites due to moisture (perspiration), oil, hair, or fur. An adhesively-applied sensor can lift away from the tissue when the subject moves or flexes, thus resulting in erroneous data. An adhesively-applied sensor requires a cable leading away from the sensor which impairs patient mobility and measurement reliability.

OVERVIEW

An example of the present subject matter includes a non-adhesive tissue oximetry sensor. A device includes a non-invasive in vivo sensor system for optical measurement or monitoring of selected blood constituents/metabolites in living tissue. In one example, the device is configured to measure light absorption at multiple wavelengths.

A device includes an oximeter having upper and lower jaws joined by a linkage having an elastic element, such as a spring. The linkage, or joint, can be configured for a particular application and in various examples, is configured to enable two degrees of freedom (such as pitch and heave or any other two such degrees), three degrees of freedom (such as pitch, heave, yaw or roll), four degrees of freedom (pitch, heave, roll, and yaw), or more than four degrees of freedom. Various examples are configured to conform to a variety of anatomical shapes and sizes, and are, in particular, configured to measure a physiological parameter associated with the thenar eminence.

In one example, upper and lower jaws form a clamp device. The elastic element exerts a force to securely hold the device in contact with the thenar eminence or other tissue site. A user can overcome the force and disengage the device from the tissue site.

An example of the device can adapt to the shape of the body part and apply a uniform pressure to the tissue at the measurement site. A uniform pressure can enable accurate measurement using the optical sensor. The device can be sized or otherwise configured to enable measurement of various sites, including, for example, a calf, a forearm, a foot, an animal limb, or other structure.

In various examples, one or both of the jaws provide a structure for coupling to or for affixing various components or other elements, including an optical sensor, circuitry (or programming) for determining a physiological measurement (including arterial oximetry or tissue oximetry), a power supply, a communication module (wired or wireless), a display, and power control circuitry (to detect the presence of tissue and automatically transition between a sleep mode and a powered mode).

Other configurations are also contemplated, including an example that provides pulse oximetry or regional oximetry, an example that includes a temperature sensor, and an example having a silicone gripping surface proximate the sensor element.

A device includes a clamp and a sensor. The sensor can be permanently attached to the clamp, temporarily attached to the clamp, or held in place between a jaw of the clamp and a tissue by the force exerted by the clamp. The clamp includes a first jaw member and a second jaw member. The first jaw member has a jaw face and the second jaw member has a complementary face. The second jaw member is held in alignment with the first jaw member by a joint. The joint has an elastic member configured to exert a compressive force between the jaw face and the complementary face. In various examples, the joint is configured to allow movement of the jaw face relative to the complementary face in directions corresponding to pitch, roll, yaw, heave, or any combination or permutation thereof. In one example, the compressive force is substantially uniform over a surface of the jaw face. In one example, the joint, the jaw face, and the complementary face are configured to permit the jaw faces to conform to a variety of anatomically shapes and sizes and to distribute the compressive force over the jaw faces. The contact surface of the sensor can conform, or adapt, to an irregular surface of the tissue. In one example, mechanical forces exerted on the sensor are uniformly distributed based on conformance of the sensor with the tissue. The force is distributed in the sense that it is dispersed through a space or over an area (the surface area). The sensor is coupled to the jaw face or held in place by a compressive force of the jaw face. The sensor is configured to generate a sensor signal corresponding to a physiological parameter of tissue proximate the jaw face.

The device can be coupled to the thenar eminence and configured to generate a measure of a physiological parameter. In one example, the device can be repositioned and provides good tissue contact and good measurement reliability.

In one example, the device is portable and includes an integrated processor module (such as analog or digital circuitry), a display, a power source, and a wireless communications module.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different later suffixes may represent different instances of similar components. The drawings illustrate generally, by way of example, but not by way of limitation, various embodiments discussed in the present document.

FIGS. 4A and 4B illustrate views of an elastic element according to one example.

FIGS. 5A, 5B, and 5C illustrate views of a device according to one example.

DETAILED DESCRIPTION

Figure 1:
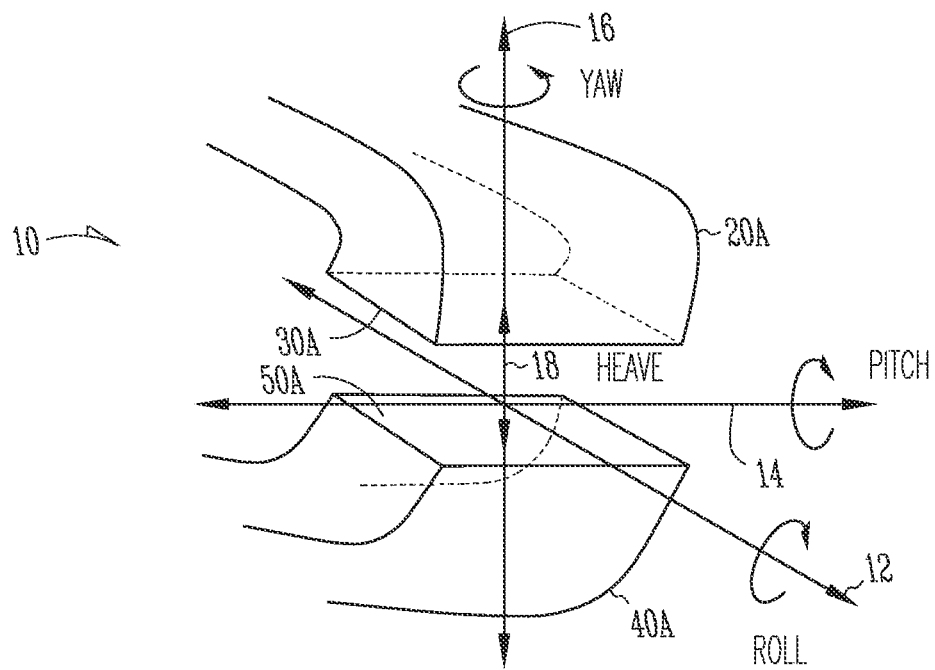
FIG. 1 illustrates a coordinate system.

FIG. 1 illustrates coordinate system 10 suitable for use in describing selected examples of the present subject matter. System 10 includes orthogonal axes 12, 14, and 16, for which rotation about each is deemed roll, pitch, and yaw, respectively. In addition, a translational heave motion is along axis 16, as denoted by reference 18.

Pitch refers to motion that can be viewed as tilting forward or backward. Roll refers to motion that can be viewed as tilting side to side. Yaw refers to motion that can be viewed as turning left or right. Heave refers to motion that can be viewed as moving up and down along a linear path.

The figure also depicts a portion of a device according to one example. A first jaw piece is shown at 20A and includes jaw face 30A. Second jaw piece 40A and includes jaw face 50A. The axes illustrated have an origin located between the jaw faces 30A and 50A, however, this is merely for example and it is understood that any particular axis can pass through space without regard to whether or not it intersects with the device.

Figure 2A:
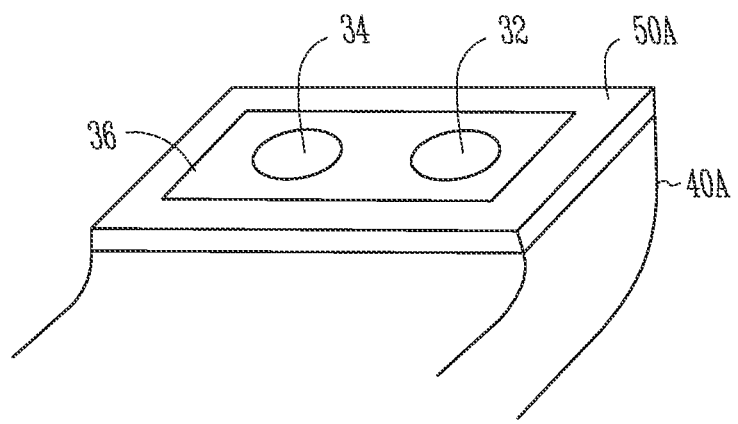
FIGS. 2A and 2B illustrate a jaw face with a sensor according to two examples.

FIG. 2A illustrates a view of sensor 36 affixed to jaw face 50A according to one example. In this example, jaw face 50A includes sensor elements 32 and 34. Sensor elements 32 and 34 can include an optical emitter, an optical detector, a temperature sensor, or other component configured for measurement of a physiological parameter. In this example, sensor 36 can be considered as permanently coupled to jaw face 50A.

Figure 2B:
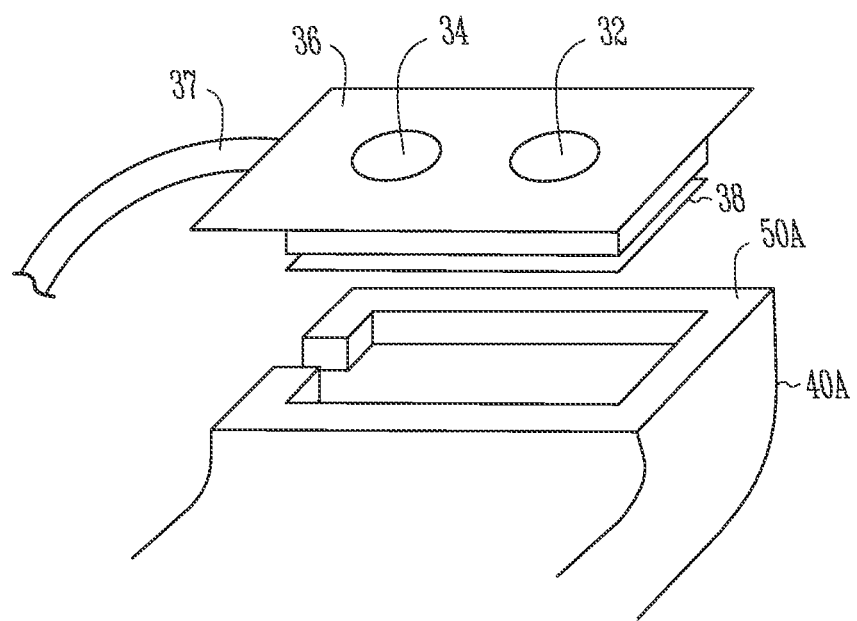

FIG. 2B illustrates an exploded view of sensor 36, adhesive layer 38, jaw face 50A, and jaw piece 40A. In one example, adhesive layer 38 couples sensor 36 to jaw face 50A. In one example, adhesive layer 38 is omitted and the sensor is retained by pressure exerted by jaw face 50A on the tissue. In these examples, sensor cable 37 is coupled to the sensor at one end and coupled to a secondary device (such as an external monitor) at a second end. In this example, sensor 36 can be considered as temporarily coupled to jaw face 50A.

Figure 3A:
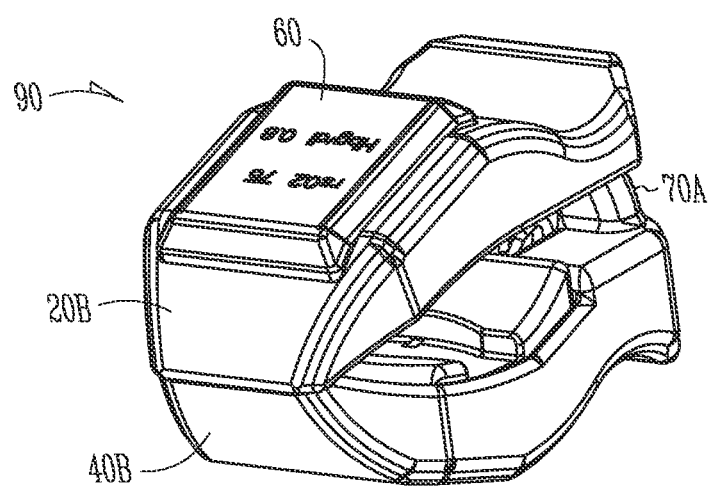
FIG. 3A illustrates a perspective view of a device according to one example.

FIG. 3A illustrates a perspective view of device 90 according to one example. Device 90 is configured for four degrees of freedom (DOF) to accommodate a variety of tissue contours or sizes. In particular, device 90 is suitable for use at a thenar eminence area.

Device 90 includes display 60 coupled to jaw piece 20B. Jaw piece 20B is coupled to jaw piece 40B by joint 70A. Joint 70A allows relative movement corresponding to pitch, roll, yaw, and heave.

Figure 3B:
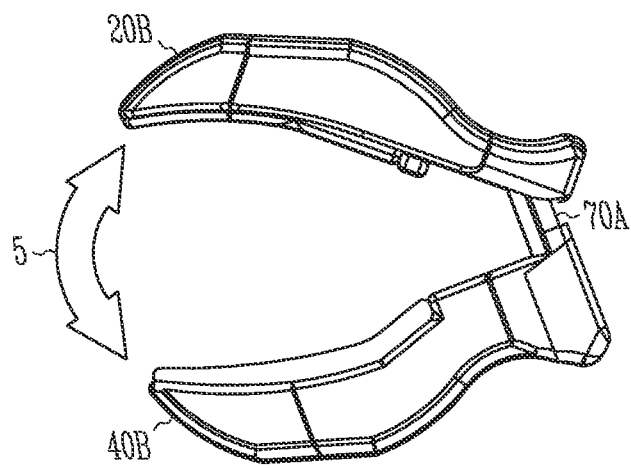
FIG. 3B illustrates an elevation view of a device with an indication of movement about a pitch axis according to one example.

FIG. 3B illustrates an elevation view of a device with an indication of movement about a pitch axis according to one example. Joint 70A allows movement of jaw piece 20B and jaw piece 40B in a direction indicated by arrow 5. Jaw piece 20B and jaw piece 40B can open and close. In one example, joint 70A includes an elastic element, such as a spring, that urges jaw piece 20B and jaw piece 40B towards a closed for contracted) position. A user can manipulate jaw pieces 20B and 40B to overcome the force exerted by the elastic element and open the jaw pieces to allow the device to be attached or released from the tissue site.

As shown in FIG. 3B, jaw piece 20B and jaw piece 40B each has a tail portion that extends to the right of the pivot provided by joint 70A. The tail portions can be manipulated by a user in a manner in which they are drawn together and thereby open the jaw to allow repositioning or release of device 90 from engagement on a tissue site. In various examples, jaw piece 20B and jaw piece 40B can be manipulated to move in directions described as heave, roll, pitch and yaw.

Figure 3C:
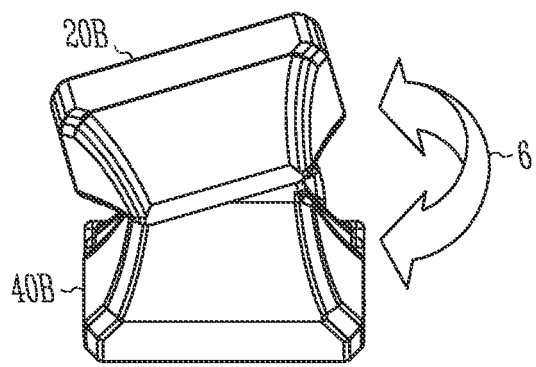
FIG. 3C illustrates a view of a device with an indication of movement about a roll axis according to one example.
Figure 3D:
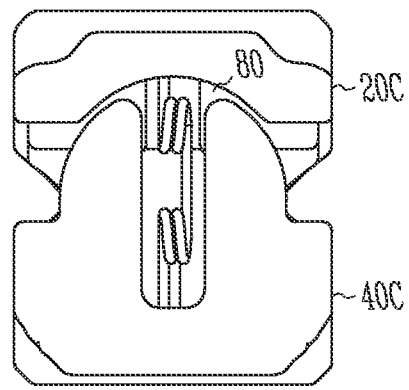
FIG. 3D illustrates a view of a device according to one example.

FIG. 3C illustrates a view of a device with an indication of movement about a roll axis according to one example. Roll refers to rotation for tilting) of the mechanism. In the figure, jaw piece 20B and jaw piece 40B are shifted about a roll axis as denoted by arrow 6. Detail 80, illustrated in FIG. 3D, denotes the gap or clearance formed by a curved feature on jaw piece 20C and a corresponding curved feature on jaw piece 40C. Detail 80 can also be referred to as a slot and enables relative movement of jaw piece 20C and jaw piece 40C about a roll axis.

Figure 3E:
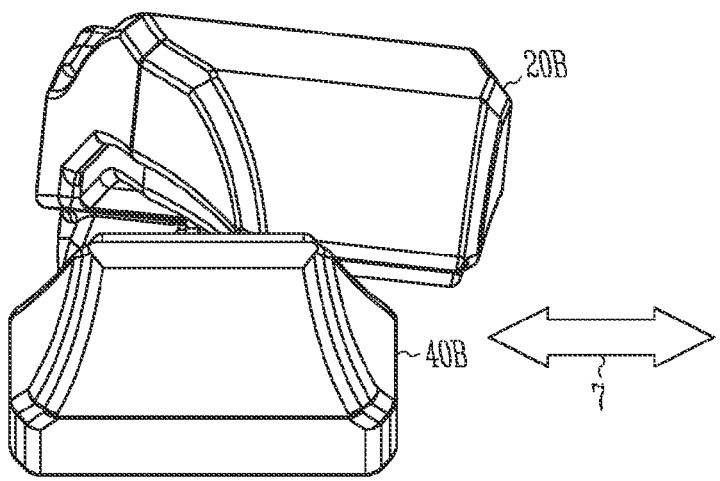
FIG. 3E illustrates a view of a device with an indication of movement about a yaw axis according to one example.

FIG. 3E illustrates a view of a device with an indication of movement about a yaw axis according to one example. Yaw denotes side to side movement of the mechanism, and as indicated by arrow 7, jaw piece 20B and jaw piece 40B are shifted on a yaw axis. In this example, the axis of rotation for yaw passes through a point offset from a jaw face.

Figure 3F:
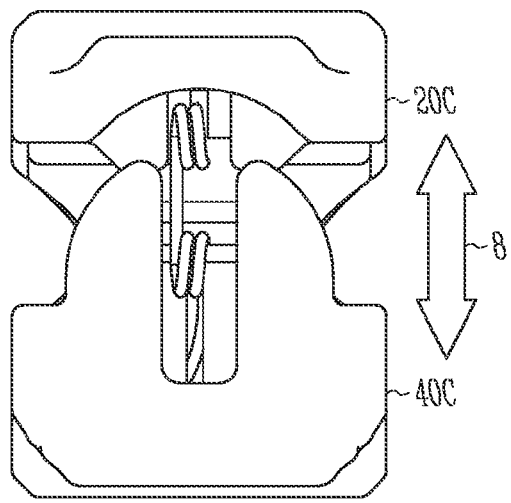
FIGS. 3F and 3G illustrate views of devices with and FIG. 3F includes an indication of translational movement (sometimes referred to as heave) according to one example.
Figure 3G:
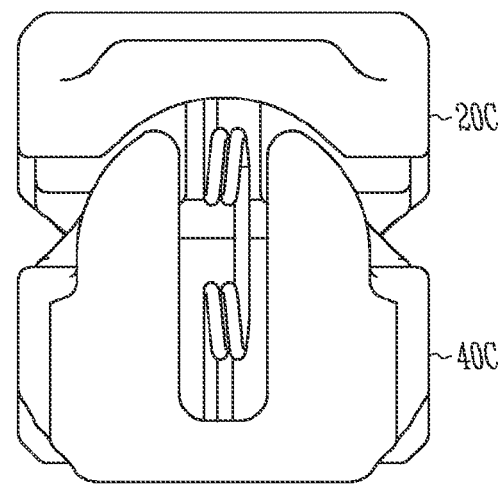

FIGS. 3F and 3G illustrate views of devices with an indication of heave according to one example. Heave refers to up and down movement along an axis. A structural feature, such as slots in the spring inserts, allows vertical movement of jaw piece 20C relative to jaw piece 40C. FIG. 3F illustrates jaw piece 20C drawn apart from jaw piece 40C and FIG. 3G illustrates the jaw pieces drawn together.

FIGS. 4A and 4B illustrate views of elastic element 100 according to one example. Elastic element 100, in the example shown, includes a spring. The spring includes double coils, a first coil which is formed on axis 102 and a second coil formed on axis 104 which differs from axis 102. Other forms of springs or elastic elements are also contemplated, including a formed clip (of metal or plastic), and an elastomeric polymer band. In various examples, the elastic element is a single component located proximate a center of the device or can be distributed among multiple locations such as at the side portions of the device. Elastic element 100, in the example shown, allows multiple degrees of freedom and is configured to provide sufficient clamping force to enable accurate measurement of a physiological parameter.

Figure 5C:
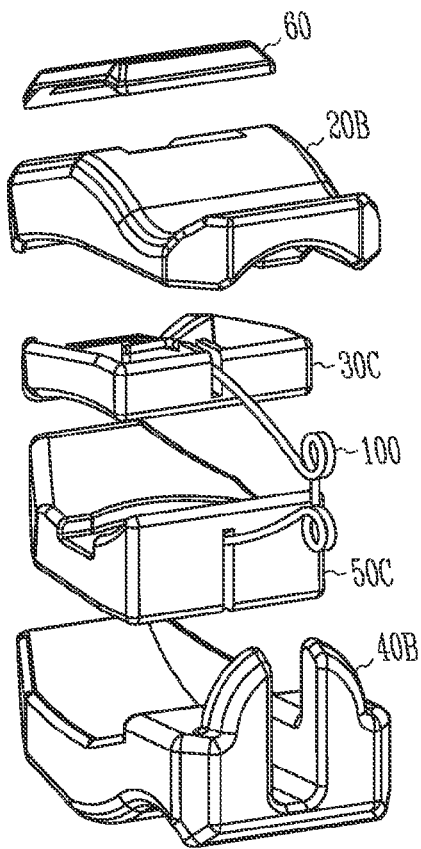

FIGS. 5A, 5B, and 5C illustrate views of a device according to one example. In this example, jaw piece 20B and jaw piece 40B are coupled by joint 70A. Joint 70A is urged towards a closed position by elastic member 100. In the example shown, jaw piece 20B carries display 60. Display 60, in various examples also includes circuitry to process the data provided by the sensor elements. For example, a sensor can be provided in jaw face 30C or jaw face 50C. Elastic element 100 is coupled to jaw faces 30C and 50C each of which is coupled to a respective one of the jaw pieces 20B and 40B. Detail 80, shown in FIG. 5B, enables motion about the roll axis. In this example, a single elastic element 100 is located proximate the center of the device and provides a force to securely clamp on the tissue. The example shown allows for four degrees of freedom, namely pitch, roll, yaw, and heave.

Figure 6A:
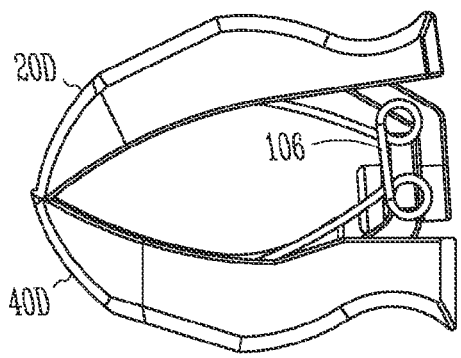
FIGS. 6A, 6B, and 6C illustrate views of a device according to one example.
Figure 6B:
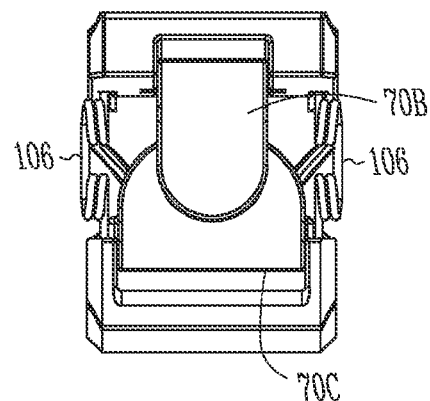
Figure 6C:
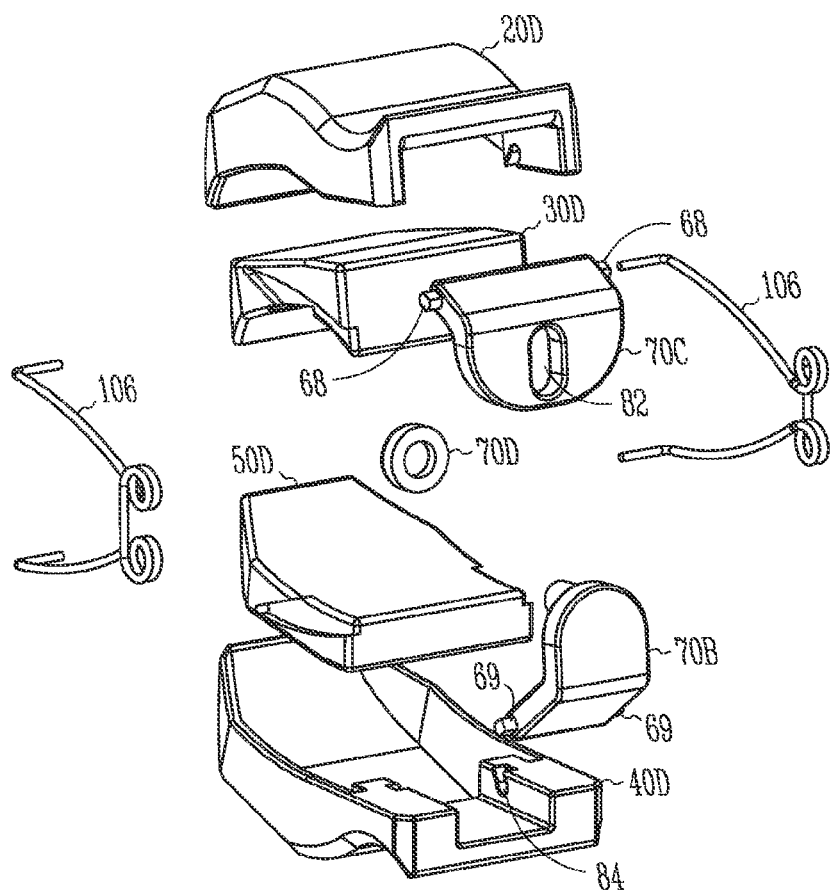

FIGS. 6A, 6B, and 6C illustrate views of a device having two hinges, according to one example. Jaw piece 20D and jaw piece 40D are urged together by elastic elements 106 located on the sides of the device. Pitch is provided by pins 68 and pins 69 of joint 70C and joint 70B, respectively. Yaw is enabled by pin 69 engagement with slot 84 shown on one side of jaw piece 40D. Roll and heave motions are enabled by joint 70B engagement with slot 82 and secured by fastener 70D. A sensor is provided in one or both of jaw face 30D and 50D. The dual hinge configuration of this example allows motion in four degrees. In particular, the dual hinges enable motion about a pitch axis and the slots, some of which are visible in FIG. 6C, allows roll movement to accommodate variations in tissue contours.

Elastic elements 106 can be replaced by other configurations, including a single elastic element near the device centerline.

Figure 7A:
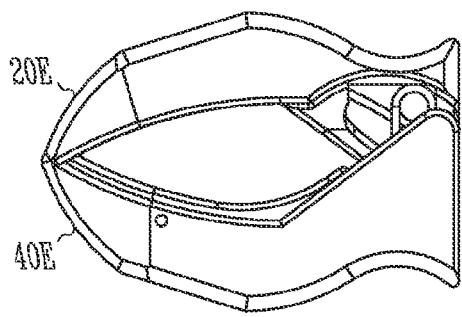
FIGS. 7A, 7B, and 7C illustrate views of a device according to one example.
Figure 7B:
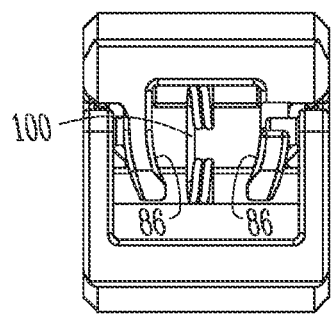
Figure 7C:
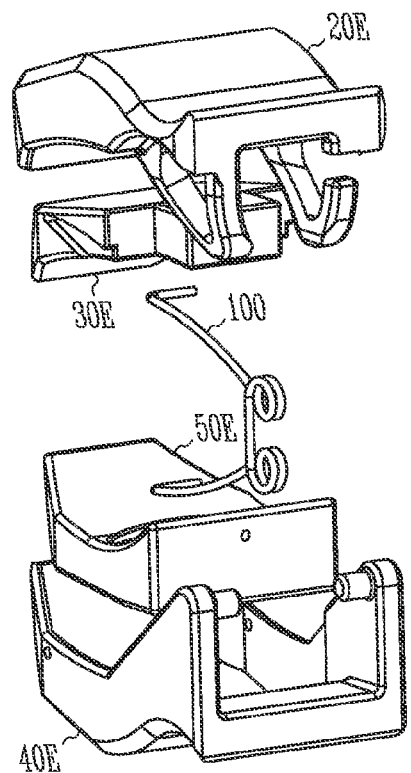

FIGS. 7A, 7B, and 7C illustrate views of a device having a joint including a flared slot, according to one example. This example enables four degrees of freedom (pitch, roll, yaw, and heave). The example shown includes jaw pieces 20E and 40E which are urged to a closed positions by elastic element 100 (FIG. 7B). Jaw faces 30E and 50E are coupled to jaw pieces 20E and 40E, respectively. Curvature associated with flared members 86 is visible in FIG. 78. In one example, members 86 are angular or straight and include sufficient clearance with mating components to enable movement having one, two, three, or four degrees of freedom.

Figure 8A:
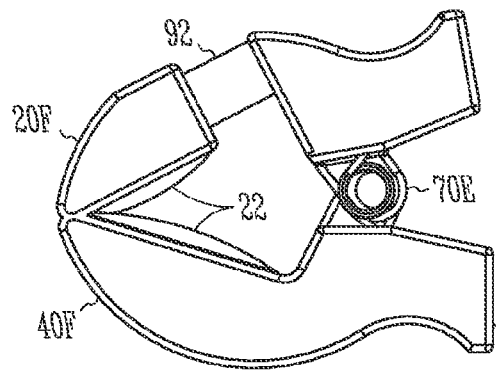
FIGS. 8A, 8B, and 8C illustrate views of a device according to one example.
Figure 8B:
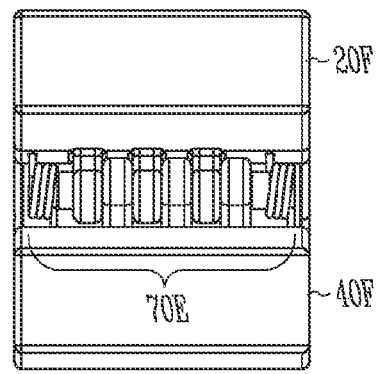
Figure 8C:
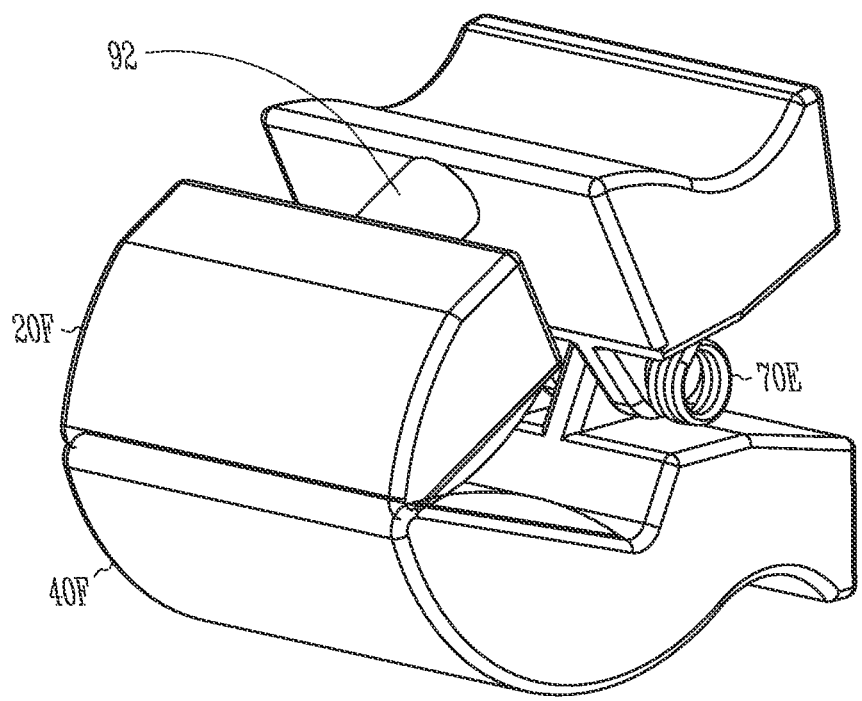

FIGS. 8A, 8B, and 8C illustrate views of a device having a rotary joint according to one example. Jaw pieces 20F and 40F are urged to a closed position by elastic elements at joint 70E. In addition, jaw piece 40F has a fixed configuration whereas jaw piece 20F includes rotary joint 92. Rotary joint 92 has an axis that enables rotation of a first end of jaw piece 20F independent of a second end of jaw piece 20F. Resilient elements 22 are provide in the example shown and enable the device to accommodate various contours of tissue. Resilient elements 22 can include a cushion of foam or silicone.

This example enables motion along two degrees of freedom. The hinge structure enables a pitch motion and jaw piece 20F enables a roll motion. An axis of rotation of joint 92 lies concentric with the cylindrical structure shown in FIG. 8A. FIG. 8B illustrates a perspective view of joint 92 about which jaw piece 20F is free to rotate.

Figure 9A:
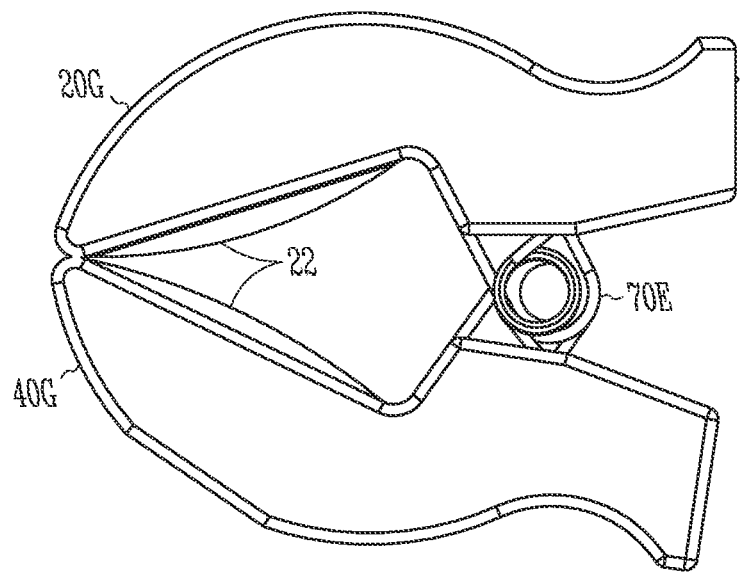
FIGS. 9A and 9B illustrate views of a device according to one example.
Figure 9B:
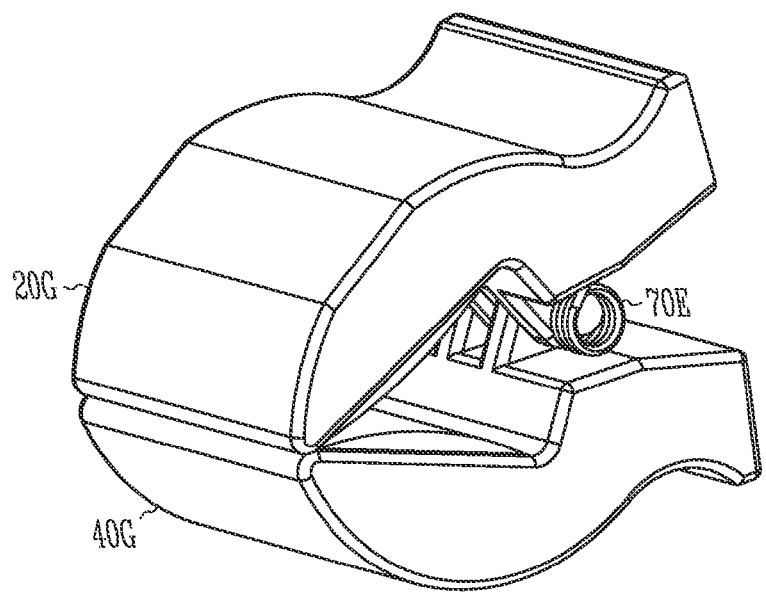

FIGS. 9A and 9B illustrate views of a device according to one example. The example shown provides a single degree of freedom of movement about the pitch axis. In the example shown, both jaw piece 20G and jaw piece 40G are fixed and each include resilient member 22. Joint 70E allows rotation about a single axis and an elastic member urges closure of the jaw pieces.

Figure 10A:
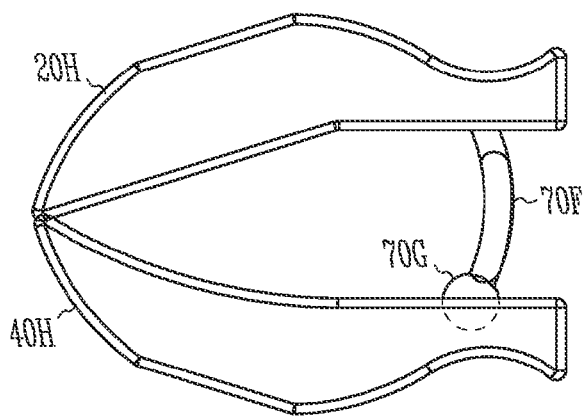
FIGS. 10A, 10B, and 10C illustrate views of a device according to one example.
Figure 10B:
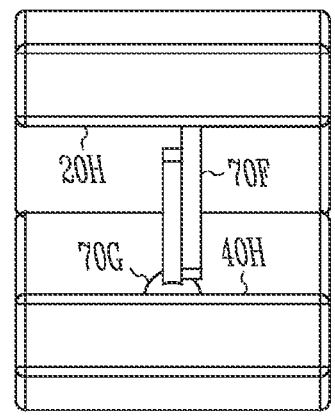
Figure 10C:
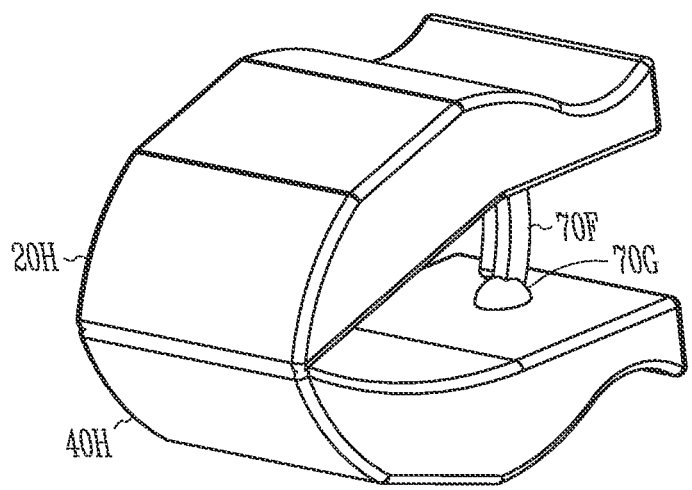

FIGS. 10A, 10B, and 10C illustrate views of a device according to one example. In this example, the joint includes ratchet 70F as well as a spherical ball joint 70G. Ratchet 70F includes a mechanism that prevents motion in one direction and allows motion in another direction. Here, ratchet 70F can be manually operated to enable closure of the jaw pieces 20H and 40H and prevent separation of the jaw pieces unless a pawl or other motion limiting component is drawn away from teeth of the ratchet. Ball joint 70G allows circular motion akin to roll, pitch, and yaw.

In this example, ratchet 70F allows adjustment of the clamping pressure. The ball joint 70G allows the assembly to conform to tissue (such as the thenar eminence) by allowing, among other things, roll and yaw.

Figures 11A, 11B:
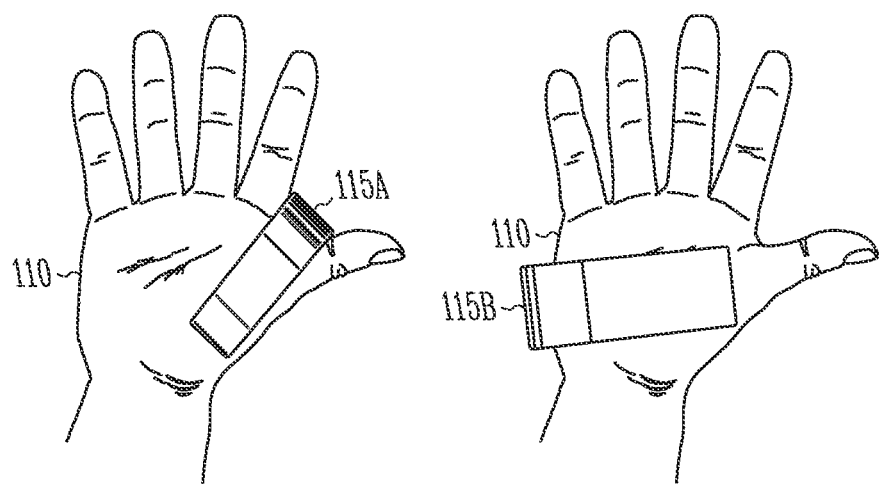
FIGS. 11A, 11B, 11C, and 11D illustrate devices relative to a human hand according to various examples.
Figure 11C:
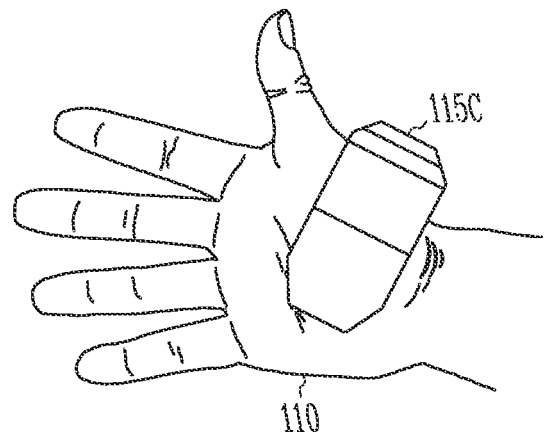
Figure 11D:
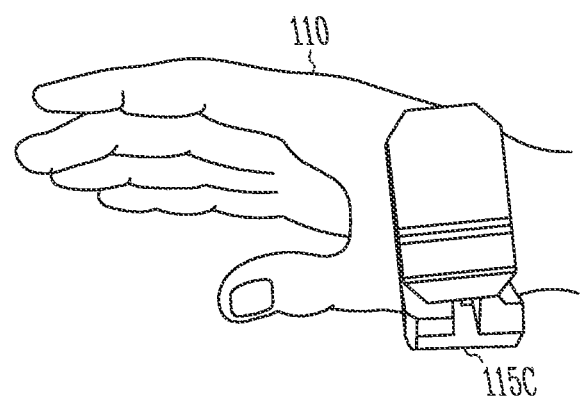

FIGS. 11A, 11B, 11C, and 11D illustrate various devices relative to a user's hand according to various examples. In each figure, the device is configured to position a sensor proximate the thenar eminence. The devices can be configured for use on either a left or a right hand. In FIG. 11A, device 115A is positioned with a joint portion of the device between a thumb and the index finger of hand 110. Device 115A is configured for motion described as having 1, 2, 3, or 4 degrees of freedom. In FIG. 11B, device 115B is positioned with a joint portion proximate the hypo-thenar eminence of hand 110. In FIG. 11C, device 115C is positioned with a joint between the thumb and the wrist. FIG. 11D illustrates another view of device 115C.

Figure 12:
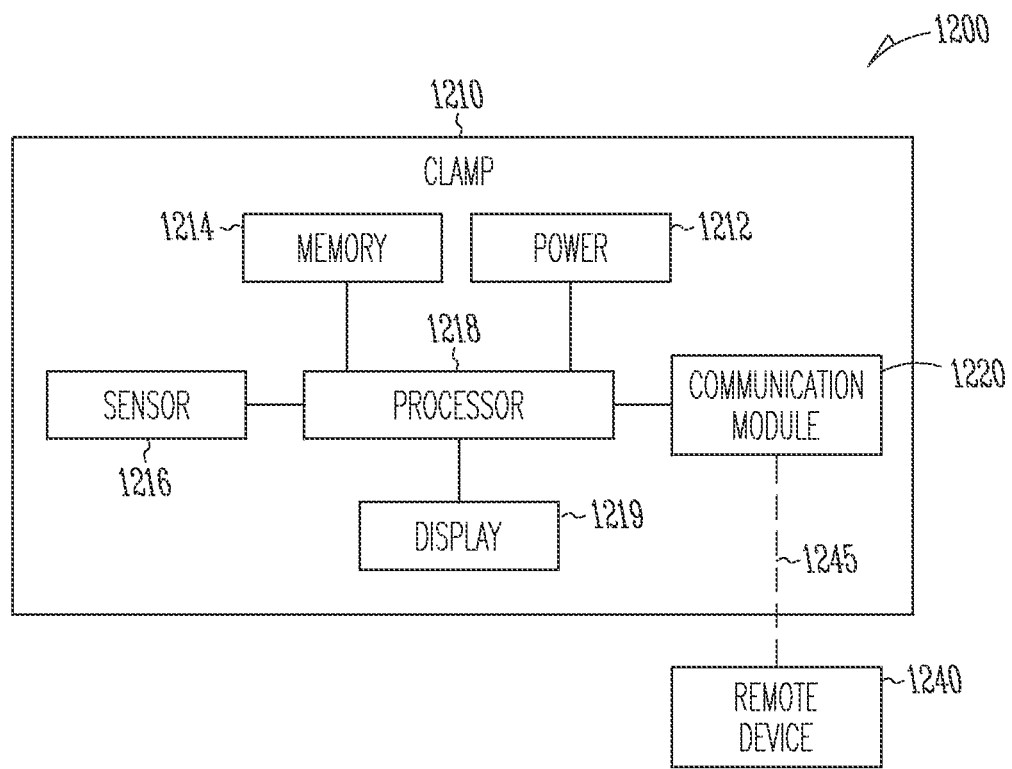
FIG. 12 illustrates a block diagram of a system according to one example.

FIG. 12 illustrates a block diagram of system 1200 according to one example. In this example, system 1200 includes device 1210 and remote device 1240. Device 1210 includes processor 1218 coupled to sensor 1216. Sensor 1216 can include one or more of an optical detector (such as a photo detector), an optical emitter (such as a light emitting diode), a temperature sensor (such as a thermistor), or other sensor configured to measure (or monitor) a physiological parameter. An output signal from sensor 1216 is coupled to processor 1218. Processor 1218, in this example, executes instructions stored in memory 1214 and uses data stored in memory 1214 to determine a result. The result can be stored in memory 1214, conveyed to communication module 1220, displayed in a human-perceivable manner on display 1219, or any combination of stored, conveyed, and displayed. Power unit 1212 provides power to any one or all of the components of device 1210. In one example, power unit 1212 includes a battery or other energy storage device. In one example, power unit 1212 includes a rechargeable battery and a recharging circuit. The recharging circuit includes a power connector configured to allow the device to be connected or docked with a recharging base unit.

Communication module 1220 can include a radio frequency (RF) transceiver (such as a Bluetooth device) or an optical coupler configured to communicate using infrared energy. Link 1245 can include an RF channel, an optical channel, or other communication channel. In one example, communication module 1220 includes a connector to enable a wired connection between processor 1218 and remote device 1240.

Remote device 1240 can include a complementary device and in various examples, includes a wirelessly-coupled processor such as a laptop computer. Remote device 1240 can be configured to store the result or can be configured to provide instructions or provide data to device 1210 via link 1245.

Processor 1218 can include a digital processor or an analog processor including an amplifier, a filter, or other circuitry.

Figure 13:
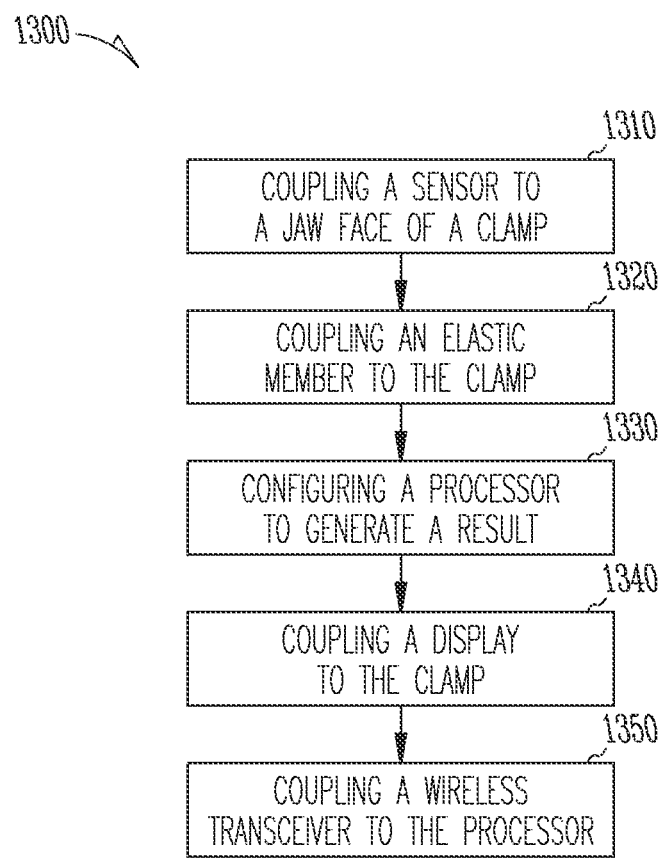
FIG. 13 illustrates a flow chart of a method according to one example.

FIG. 13 illustrates a flow chart of method 1300 according to one example. Method 1300 includes, at 1310, coupling a sensor to a jaw face of a clamp. The clamp can include any of the devices described herein or variations thereof. At 1320, method 1300 includes coupling an elastic member to the clamp. The elastic member, such as a spring, can be coupled to a joint of the device and configured to urge the closure of the clamp jaws. At 1330, method 1300 includes configuring a processor to generate a result. The result can include pulse oximetry (arterial oximetry), tissue oximetry (mixed venous), temperature, or any other measure of a physiological parameter.

At 1340, method 1300 includes coupling a display to the clamp. The display can include a display screen or one or more LED lights. At 1350, method 1300 includes coupling a wireless transceiver to the processor. The wireless transceiver can include an RE transceiver or other type of wireless communication device.

The examples illustrated and described include a variety of joints, some of which can be referred to as articulating, translating, or a prismatic.

In various examples, the device is configured to provide a distance between the joint and the sensor at the jaw face sufficient to position the sensor proximate the thenar eminence region of the hand.

The elastic element can exert a tension force or an extension force to draw the jaw pieces together. In some examples, the jaw face includes a rubber, silicone, or other surface to increase frictional resistance and retain the device in a selected position.

The present subject matter can be tailored for various configurations and thus suited for a variety of applications. For example, the sensor can be coupled to the jaw face by a combination of structural features that might be considered temporary or permanent.

A temporary coupling can allow user attachment and detachment of a sensor and a jaw face. An example of a temporary coupling is illustrated in FIG. 2B, and as noted elsewhere in this document, one example includes an adhesive. Other temporary couplings are also contemplated. For example, a temporary coupling can include a variety of combinations of structural features such as a pin, a recess, a clip, a shoulder, an interference fit, or other such elements. In one example, a temporary coupling is configured to retain the sensor in alignment relative to a jaw face or configured to constrain independent movement of the sensor relative to the jaw face. In one example, a sensor is temporarily coupled to, or retained by, the jaw face by means of a compressive force exerted by the clamp. In one example, complementary features of the sensor and of the jaw face allow the sensor to float on the jaw face. A temporary coupling can be easily assembled or disassembled by a user.

A temporary coupling may allow a user to replace a sensor or select from a variety of different sensors suited for different purposes. For example, a single clamp can be reconfigured to carry a sensor suitable for measuring temperature, electrical conductivity, or other physiological parameter. In various examples, the sensor includes one or more optical elements including an emitter and a detector. The sensor can be tailored for use at a particular optical frequency, sensitivity, range, or other characteristic. A clamp can be re-used with different patients and carry different sensors or sensor configurations depending on user requirements as to a particular measurement or monitoring application.

In one example, a sensor is replaceable and therefore, disposable. A disposable sensor is inexpensive relative to the cost associated with the compete device.

A permanent coupling does not allow user attachment and detachment of a sensor and a jaw face. An example of a permanent coupling is illustrated in FIG. 2A in which the sensor is securely affixed to the jaw face. The sensor can be coupled by a variety of structural features such as a pin, a recess, a clip, a shoulder, an interference fit, or other such element. In one example, a permanent coupling includes an adhesive configured to retain the sensor in a fixed position relative to a jaw face.

A sensor permanently coupled to a jaw face is well suited for an application corresponding to the particular sensor. A clamp can be configured to carry a sensor suited for measuring temperature, electrical conductivity, or other physiological parameter. In various examples, the sensor includes one or more optical elements including an emitter and a detector. The sensor can be tailored for use at a particular optical frequency, sensitivity, range, or other characteristic.

A jaw face can be configured to carry multiple sensors. In addition, a first sensor can be coupled to a first jaw face and a second sensor can be coupled to a complementary face. The faces and sensors can be configured for permanent or temporary coupling and the first sensor and the second sensor can be different or matching.

The jaws can be configured with a joint that allows for various combinations of freedom of movement. Using representations in which Roll=R, Pitch=P, Heave=H, and Yaw=Y, the following combinations of jaw movement are contemplated: RP, RH, RY, PH, PY, HY, RPH, RPY, RHY, PHY, and RPHY. As such, RP denotes a joint in which the combination of roll and pitch are enabled and RHY denotes a joint in which the combination of roll, heave, and yaw are enabled. Depending on the configuration of movements enabled, a joint can include structural movement limiting elements that preclude or allow movement in a particular manner.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
providing a clamp having a first jaw member coupled to a second jaw member by a joint, the second jaw member having a complementary jaw, the joint configured to enable movement of the jaw face relative to the complementary face in directions corresponding to pitch, roll, yaw, and heave;
coupling a sensor to a jaw face of the clamp, the sensor configured to generate a sensor signal corresponding to a physiological parameter of tissue proximate the jaw face; and
coupling an elastic member to the clamp, the elastic member configured to exert a compressive force between the jaw face and the complementary face, the compressive force distributed over a surface of the jaw face.

2. The method of claim 1 further including configuring a processor to generate a result based on the signal.

3. The method of claim 2 further including coupling a wireless transceiver to the processor, the wireless transceiver configured to wirelessly communicate with a remote device.

4. The method of claim 2 wherein configuring the processor includes providing program instructions to determine at least one of tissue oximetry, pulse oximetry, or temperature.

5. The method of claim 2 further including coupling a wired connector to the processor, the wired connector configured to communicate with a remote device.

6. The method of claim 1 further including coupling a display to the clamp, the display configured to render the result in a human perceivable manner.

7. The method of claim 1 wherein coupling the sensor to the jaw face includes providing an optical emitter and an optical detector.

8. The method of claim 1 wherein coupling the elastic member includes engaging a spring.

* * * * *